United States Patent [19]

Trybulski et al.

[11] Patent Number: 5,346,910
[45] Date of Patent: Sep. 13, 1994

[54] MALEIMIDE DERIVATIVES OF OXOTREMORINE

[75] Inventors: Eugene J. Trybulski, Park Ridge, N.J.; Herbert J. Brabander, Nanuet, N.Y.

[73] Assignee: American Cyanamid Company, Wayne, N.J.

[21] Appl. No.: 893,146

[22] Filed: Jun. 3, 1992

[51] Int. Cl.$^5$ ............... A61K 31/445; A61K 31/40; C07D 207/40
[52] U.S. Cl. ................... 514/326; 514/422; 514/425; 546/208; 548/406; 548/518; 548/519; 548/520; 548/524; 548/546
[58] Field of Search ............... 548/518, 519, 520, 524, 548/546, 406; 546/208; 514/326, 422, 425

[56] References Cited

U.S. PATENT DOCUMENTS

| | | | |
|---|---|---|---|
| 4,937,235 | 6/1990 | Trybulski | 514/63 |
| 4,952,600 | 8/1990 | Trybulski | 514/424 |
| 5,001,142 | 3/1991 | Trybulski | 514/422 |
| 5,025,099 | 6/1991 | Trybulski | 548/527 |

OTHER PUBLICATIONS

Svensson, U., Acta., Pharm. Succ. 15: 67–70, (1978), Acetylene . . . value.
Ringdahl, B., J. Med. Chem., 31: 683–688, (1988), 5-methyl-2-pyrrolidone . . . Agonists.
Carson, S., Febs Letters, 109: 81–84, (1980), Differential Effect . . . Membranes.
Bartus, R., Psychopharmacology Bulletin, 19(2): 168–184, (1983), An Evaluation . . . Humans.
Christie, J. E., Brit. J. Psychiat., 138: 46–50, (1981), Physostigmine . . . Dementia.
Vickroy, T. W., J. Pharm. Exper. Thera., 229: 747–755, (1984), Pharmacological . . . (+)-[$^3$H]Cismethyldioxolane.
Ringdahl, B., "Structural Determinants of Muscarinic Agonist Activity", The Muscarinic Receptors, J. H. Brown Ed Humana Press, Clifton, N.J., 151–218, (1989).
Watson, M., J. Pharm Exper. Thera., 237: 419–427, (1986), [$^3$H]Pirenzepine . . . Subtypes.
Coyle, J. T., Science, 219: 1184–1190, (1983), Alzheimer's . . . Innervation.
Bonner, T. I., Science, 237: 527–532, (1987), Identification . . . Genes.
Bartus, R. T., Neurobiology of Aging, 1: 145–152, (1980), Memory . . . Cholinomimetics.
CA 44857w Acetylene . . . maleimides. Class . . . agents. Karlen et al., p. 266, 1970.

*Primary Examiner*—Mary C. Lee
*Assistant Examiner*—Joseph K. McKane
*Attorney, Agent, or Firm*—Kenneth J. Dow

[57] ABSTRACT

Maleimide derivatives of oxotremorine and their alkylthiol addition products having the general formulae:

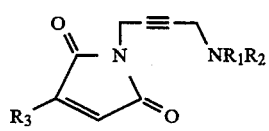

I

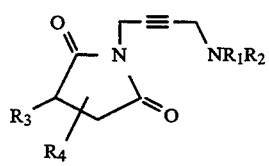

II wherein $R_1$ and $R_2$ are independently alkyl, hydroxyalkyl, acyloxy, trialkylsilyloxy or $R_1$ and $R_2$ taken together are substituted or unsubstituted pyrrolidine or piperidine, and pharmaceutical compositions for the treatment of central cholinergic disfunction.

4 Claims, No Drawings

MALEIMIDE DERIVATIVES OF OXOTREMORINE

BACKGROUND OF INVENTION

The invention relates to compounds, pharmaceutical compositions and to the use of the compounds for the manufacture of pharmaceuticals.

A chronic deficiency in central cholinergic function has been implicated in a variety of neurologic and psychiatric disorders, including senile dementia of the Alzheimer's type (SDAT), tardive dyskinesia, Pick's disease and Huntington's chorea. Postmortem neurochemical investigations of patients with SDAT have demonstrated a reduction in presynaptic markers for acetylcholine utilizing neurons in the hippocampus and the cerebral cortex [E. K. Perry, R. H. Perry, G. Blessed, B. E. Tomlinson, J. Neurol. Sci., 34, 247, (1976)]. The basis for the cholinergic abnormality is unclear, but evidence suggests that the cholinergic neurons in the nucleus basalis of Meynert may selectively degenerate in SDAT [J. T. Coyle, D. J. Price, M. R. DeLong, Science, 219, 1184, (1983)]. If this degeneration plays a role in behavior symptoms of the disease, then a possible treatment strategy would be to compensate for the loss of cholinergic output to the cortex and hippocampus.

In an aged monkey animal model, designed to mimic the symptoms of SDAT, the direct muscarinic agonists arecoline [R. T. Bartus, R. L. Dean, B. Beer, Neurobiology of Aging, 1, 145, (1980)] and oxotremorine [R. T. Bartus, R. L. Dean, B. Beer, Psychopharmacology Bulletin, 19, 168, (1983)] produced significant improvement in performance. These results in aged monkeys were corroborated in SDAT patients with arecoline which produced a more consistent improvement when compared to the anticholinergic inhibitor physostigmine [J. E. Christie, A. Shering, J. Ferguson, A. M. Glen, British Journal of Psychiatry, 138, 46, (1981)].

These animal behavioral and clinical results have instigated significant efforts in a search for a muscarinic agonist which will selectively compensate for the loss of cholinergic input in the hippocampus and cerebral cortex. However, the search must be refined to seek agonists which will not affect significantly the remaining body cholinergic functions. The recent disclosure that muscarinic receptors are not all the same but exist as a heterogeneous population of receptors substantiates the possibility for the discovery of a selective muscarinic agonist [T. I. Bonner, N. J. Buckley, A. C. Young, M. R. Brann, Science, 237, 527, (1987)].

The methodical methylation of the muscarinic agonist oxotremorine and its derivatives has been studied in the search for a selective muscarinic agonist [B. Ringdahl, J. Med. Chem., 31, 683, (1988); B. Ringdahl, "Structural Determinants of Muscarinic Agonist Activity" The Muscarinic Receptors, J. H. Brown Ed., The Humana Press, Clifton, N.J., 1989, 151]. The methodical substitution of a methyl group onto oxotremorine can probe the steric non-polar environment of the muscarinic agonist for its neurotransmitter-receptor-complex.

The present invention describes the preparation of maleimide derivatives of oxotremorine and their alkylthiol addition products which go beyond the initial study of Ringdahl. In addition to exploring the steric environment of the muscarinic agonist for its neurotransmitter complex, the maleimide and substituted maleimide compounds of the present invention may be capable of covalently interacting with auxiliary polar functionalities, such as thiol residues, within the muscarinic receptor complex. The formation of these covalent ligand-receptor complexes may be useful in the characterization and purification of the corresponding receptor.

SUMMARY OF THE INVENTION

This invention is concerned with new compounds of formulae I, II, III and IV which have cholinergic activity; with methods of treating diseases of the central nervous system in mammals employing these new compounds; with pharmaceutical preparations containing these compounds; and with processes for the production of these compounds. The compounds of the present invention may be represented by the following structural formulae I, II, III and IV:

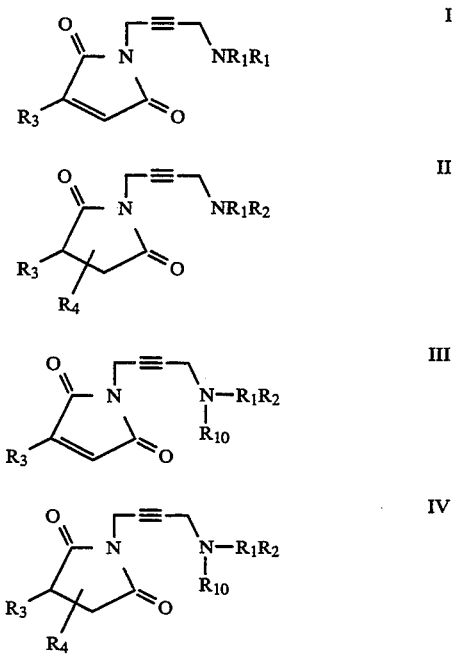

wherein $R_1$ and $R_2$ are independently selected from straight and branched $(C_1-C_6)$alkyl; or $R_1$ is selected from straight and branched $(C_1-C_6)$alkyl and $R_2$ is —$(CH_2)_nR_9$ where $n=2-6$ and $R_9$ is selected from hydroxy, $(C_1-C_{10})$acyloxy, and trialkylsilyloxy or $R_1$ and $R_2$ taken together with their associated N(itrogen) are selected from the group consisting of pyrrolidine, piperidine and moieties of the formula:

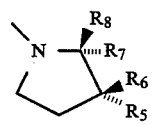

wherein $R_5$ and $R_6$ are independently selected from $(C_1-C_{10})$acyloxy, $(C_1-C_6)$alkoxy, aroyloxy, substituted aroyloxy, hydroxy, thio, $(C_1-C_6)$alkylthio, $(C_1-C_6)$alkyldithio, $(C_1-C_{10})$acylthio and hydrogen, and $R_7$ and $R_8$ are selected from hydrogen; substituted methyl where the substituting moiety is selected from hydroxy, halo (wherein halo is bromine, chlorine or ioaine) and $(C_1-C_6)$ alkylsulfonyloxy or phenylsulfonyloxy with the proviso that only one of $R_5$, $R_6$, $R_7$, or $R_8$ can be a substituent other than hydrogen;

$R_3$ is selected from hydrogen, straight and branched $(C_1-C_6)$alkyl;

$R_4$ is selected from hydrogen, straight and branched $(C_1-C_6)$alkylthio;

$R_{10}$ is selected from straight and branched $(C_1-C_6)$alkyl; and the pharmacologically acceptable salts thereof.

For the purposes herein, "aroyloxy" and "substituted aroyloxy" means a radical of the formula RCOO— where R is an aromatic monocyclic or bicyclic moiety where each ring has 5 or 6 carbon atoms such as phenyl, benzyl, naphthyl and equivalents thereof and where the substituting moiety is hydroxy, halo, alkyl $(C_1-C_6)$, alkoxy $(C_1-C_6)$, and equivalents thereof.

DESCRIPTION OF THE INVENTION

The novel compounds, represented by formulae I, II, III and IV of the present invention,

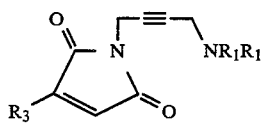

I

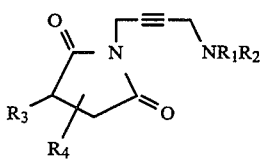

II

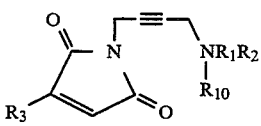

III

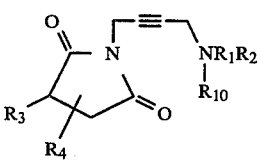

IV may be readily prepared in accordance with one or more of the following reaction Schemes wherein $R_1$ and $R_2$ are selected from straight and branched $(C_1-C_6)$alkyl; or $R_1$ is a straight or branched $(C_1-C_6)$alkyl and $R_2$ is —$(CH_2)_nR_9$ where n=2-6 and $R_9$ is selected from hydroxy, $(C_1-C_{10})$acyloxy, trialkylsilyloxy or $R_1$ and $R_2$ taken together with their associated N(itrogen) are selected from the group consisting of pyrrolidine, piperidine or moieties of the formula:

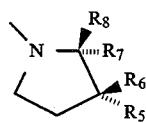

wherein $R_5$ and $R_6$ are independently selected from $(C_1-C_{10})$acyloxy, $(C_1-C_6)$alkoxy, aroyloxy, substituted aroyloxy, hydroxy, thio, $(C_1-C_6)$alkylthio, $(C_1-C_6)$alkyldithio, $(C_1-C_{10})$acylthio or hydrogen; and $R_7$ and $R_8$ are selected from hydrogen, substituted-methyl wherein the substituting moiety is selected from hydroxy, halo (wherein halo is bromine, chlorine or iodine) alkylsulfonyloxy and substituted phenylsulfonyloxy; with the proviso that only one $R_5$, $R_6$, $R_7$, or $R_8$ can be a substituent other than hydrogen;

$R_3$ is selected from hydrogen, straight and branched $(C_1-C_6)$alkyl;

$R_4$ is selected from hydrogen, straight and branched $(C_1-C_6)$alkylthio; and $R_{10}$ is selected from straight and branched $(C_1-C_6)$alkyl.

Scheme 1

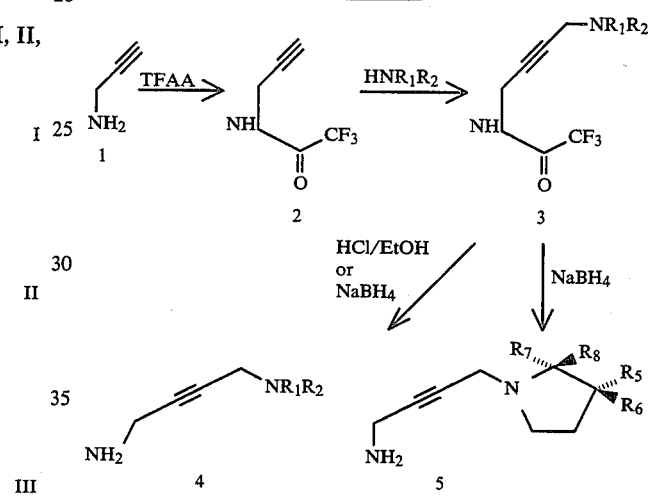

In accordance with Scheme I, the diamines of general formula 4 and 5 are prepared by a modification of previously described methods [U. Swenson, U. Hacksell, R. Dahlboom, Acta Pharm. Suec., (1978), 15, 67; H. Bittiger, J. Heid, U.S. Pat. No. 3,354,178 (1967)]. The advantage over the published procedures, is the mild conditions used to remove the trifluoroacetamide protecting group.

Propargylamine 1 is treated with trifluoroacetic acid anhydride in a solvent such as diethyl ether, tetrahydrofuan or methylene chloride to afford trifluoroacetamide 2. Compound 2 is reacted with paraformaldehyde, acetic or propanoic acid, cuprous halide and a secondary amine such as pyrrolidine, dimethylamine, piperidine, (R)-3-acetoxypyrrolidine or (S)-2-[[(1,1-dimethylethyl)dimethylsilyl]oxymethylpyrrolidine in an ethereal solvent such as diethyl ether, tetrahydrofuran or dioxane at the reflux temperature of the solvent to give the amine of general formula 3. A compound of general formula 3 is reacted in an alcohol solvent such as methanol, ethanol or isopropanol containing a mineral acid to produce a diamine of general formula 4. The preferred reaction when compounds of general formula 3 contain an acid labile group, such as (S)-2-[[(1,1-dimethylethyl)dimethylsilyl]oxy]methylpyrrolidine, is treatment with sodium borohydride in an alcohol solvent to give diamines of general formula 5.

SCHEME II

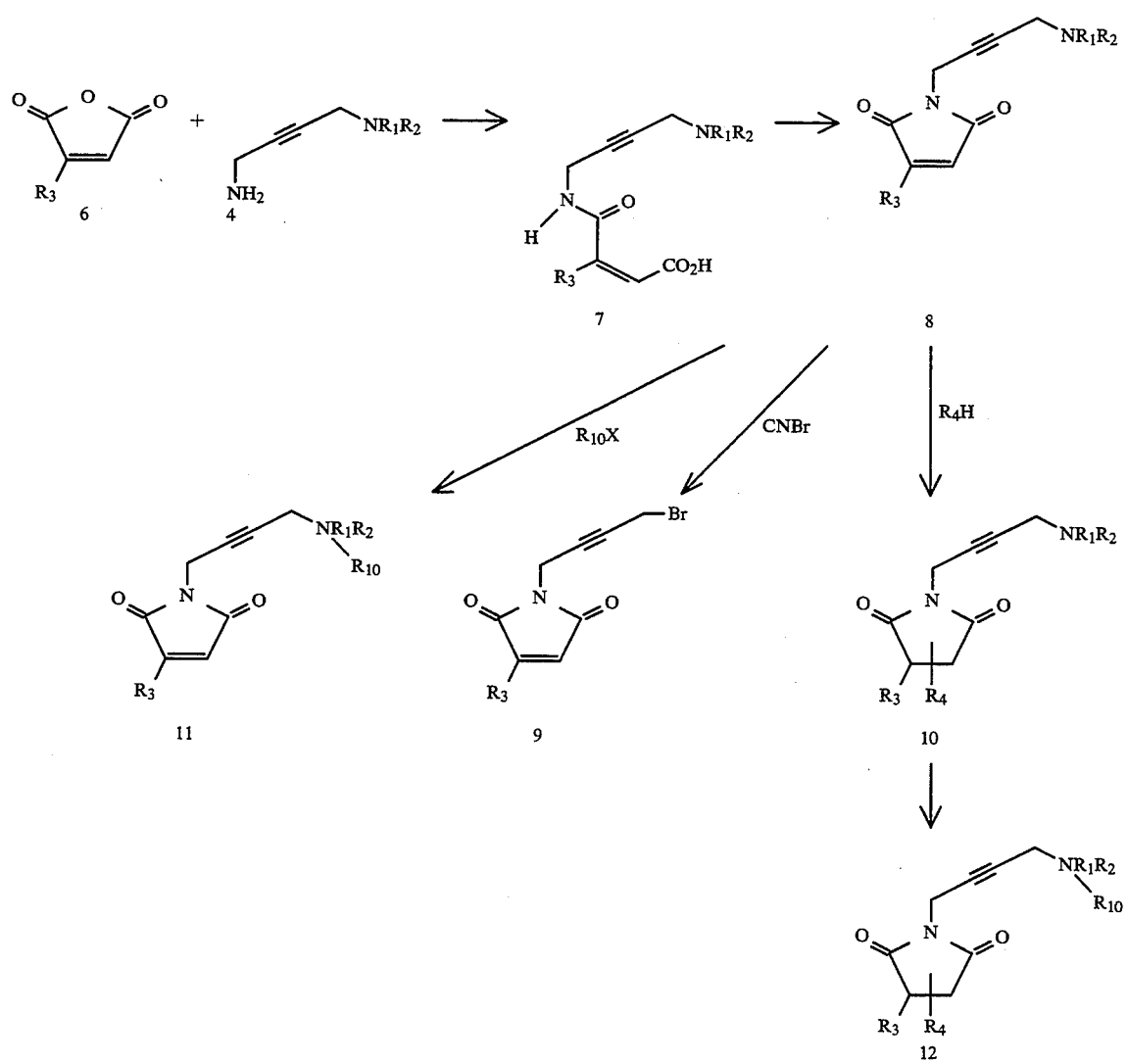

In accordance with Scheme II, a diamine of general formula is or )alkyl]substituted furane-2,5-dione 6 such as itaconic anhydride in an ether solvent such as diethyl ether or tetrahydrofuran, or in a chlorinated solvent such as methylene chloride, at from $-10°$ C. to the reflux temperature of the solvent to afford compound of general formula 7. Compounds of general formula 7 are heated without solvent or in a solvent such as toluene to approximately 100° C. or at the reflux temperature of the solvent in the presence of a catalytic amount of a strong acid such as p-toluenesulfonic acid. The product is isolated either by vacuum distillation as the product is formed or by column chromatography of the reaction mixture to give compounds of general formula 8. The reaction of a compound of general formula 8 with cyanogen bromide in an ether solvent such as diethyl ether at from $-20°$ C. to the reflux temperature of the solvent results in the formation of compounds of general formula 9. Compounds of general formula 8, are reacted with an $(C_1-C_6)$alkylthio in an ether solvent such as diethyl ether or a chlorinated hydrocarbon solvent such as methylene chloride to give products of general formula 10. Compounds of general formula 8 and 10 are reacted with a $(C_1-C_6)$alkyl halide in an ether solvent 5 maleimide such as diethyl ether or a chlorinated hydrocarbon solvent such as methylene chloride, to give the corresponding aminium salts, 11 and 12.

Also included within the present invention are the deuterium ($^2$H) tritium ($^3$H), carbon ($^{13}$C) or carbon ($^{14}$C) radiolabeled forms of the compounds of formulae I, II, III or IV. Specifically included are those compounds of formulae I and III wherein an ($^1$H) hydrogen atom in the $R_1$ or $R_2$ substituents is substituted with deuterium ($^2$H) or tritium ($^3$H) or a ($^{12}$C) carbon in the $R_1$ or $R_2$ substituent is substituted with carbon ($^{13}$C) or carbon ($^{14}$C) isotope. Also included are those compounds of formula I and III wherein $R_1$ and $R_2$ taken together are substituted or unsubstituted pyrrolidine or piperidine, as defined above, wherein at least one ($^1$H) hydrogen is substituted with deuterium ($^2$H) or tritium ($^3$H).

In a preferred embodiment, compounds of Formula I are contemplated wherein $R_1$ and $R_2$ are selected from straight and branched $(C_1-C_6)$ alkyl or $R_1$ and $R_2$ taken together with their associated nitrogen are selected from pyrrolidine and piperidine and $R_3$ is selected from hydrogen, straight and branched $(C_1-C_6)$ alkyl.

The present invention describes the preparation of maleimide derivatives of oxotremorine having muscarinic agonist activity. The maleimide and substituted maleimide derivatives described in the present invention are intermediates for the preparation of target structures and also act as muscarinic receptor ligands and can have utility by covalently interacting with auxiliary polar functionalities, such as thiol residues, within the muscarinic receptor complex. The formation of these covalent ligand-receptor complexes may be useful in the characterization and purification of the corresponding receptor.

Oxotremorine is a mimic of the natural neurotransmitter, acetylcholine, which is capable of activating the acetylcholine muscarinic receptor (agonist-like effect). The oxidation of the pyrrolidinone ring in oxotremorine to a succinimide moiety has been reported and the resulting molecule retains much of the agonist-like properties of oxotremorine (Ringdahl, B. "Structural Determinants of Muscarinic Agonist Activity", in *The Muscarinic Receptors*, ed. Brown, J. H., The Humana Press, Clifton, N.J., 1989, p184). Further oxidation of succinimide, a formal dehydrogenation, can be achieved to produce a maleimide moiety which when incorporated into the oxotremorine structure can provide a useful reagent to characterize and possibly purify the muscarinic receptor. The preparation of the maleimide derivative of oxotremorine can be easily modified to incorporate a radioactive isotope ($^3$H or $^{14}$C) to facilitate its use as a biochemical tool.

The maleimide moiety contains a highly reactive electrophilic center and is capable of chemically reacting with nucleophiles, such as sulfhydryl groups, to form a covalent bond. For example N-ethylmaleimide is a biochemical tool used to label the free sulfhydryl groups in cysteine amino acid residues present in proteins (Carson, S., FEBS Lett., 1980, 109, 81). This reagent will react with all accessible sulfhydryl groups present in an enzyme or receptor protein complex. In order to transform a non-selective reagent, such as N-ethylmaleimide, into a reagent that can distinguish amongst a number of different sulfhydryl groups, functionality must be appended onto the maleimide moiety to allow recognition of the particular environment of a specific sulfhydryl group.

The oxotremorine derivative which has been modified to incorporate the maleimide moiety contains such a functionality capable of recognizing both the acetylcholine agonist binding site and the reagent to react with any sulfhydryl groups at or near the agonist binding site.

[$^3$H] Quinuclidinyl Benzilate Binding Assay

This assay is utilized in conjunction with the $^3$H-Cis-methyldioxolane binding assay to evaluate antagonist and high affinity agonist binding properties of CNS cholinergic agents. The procedure was adapted from Watson, M., Yamamura, H. I., and Roeske, W. R., J. Pharmacol. Exp. Ther. 237: 411–418 (1986) and Watson, M., Roeske, W. R., and Yamamura, H. I., J. Pharmacol. Exp. Ther. 237: 419–427 (1986).

Tissue Preparation

Rats are sacrificed by decapitation and the brain removed and placed on ice. The cerebral cortex is dissected on a cold stage, weighed and homogenized (Polytron, setting 5.5 with PT-10 saw-tooth generator for 15 seconds) in 50 volumes (wet wt/vol) of ice-cold 10 mM (8.1 mM $Na_2HPO_4$, 1.9 mM $KH_2PO_4$) sodium-potassium phosphate buffer (NaKPB), pH 7.4. The homogenate is placed in an ice bath for 30 seconds and homogenized again as above. This procedure is repeated once again for a total of three times. The resulting homogenate is then diluted 1:3000 (original wet wt/vol) with ice-cold NaKPB for use in the assay. The final protein content per 2.0 ml of incubation mixture is 0.1 mg.

Dilution of Compounds

A stock solution of Atropine is prepared at 0.2 mM to define non-specific binding (11M final conc). Test compounds are prepared at 40 mM (final conc 1 mM) in buffer (if water soluble) or in absolute ethanol—1N HCl (1:1, v/v) and serially diluted to the desired concentrations. In general, dose-response profiles are examined between 1 mM and 1 pM final concentrations.

Preparation of $^3$H-QNB $^3$H-QNB (NEN, NET-656; specific activity=30.0 Ci/mmol) is diluted to 5 nM, with NaPB (final concentration=0.25 nM activity 18,000 cpm at a counting efficiency of 55%).

$^3$H-QMB Binding Assay

A typical protocol is outlined below:

| Tube No. | ID* | Buffer μL | Atropine μL | Test Compound μL | $^3$H—QNB μL | Tissue ml |
|---|---|---|---|---|---|---|
| 1–2 | Total | 50 | — | — | 100 | 1.85 |
| 3–4 | NS | 40 | 10 | — | 100 | 1.85 |
| 5–6 | 4e-11 | — | — | 50 | 100 | 1.85 |
| 7–8 | 4e-10 | — | — | 50 | 100 | 1.85 |
| 9–10 | 4e-09 | — | — | 50 | 100 | 1.85 |
| 11–12 | 4e-08 | — | — | 50 | 100 | 1.85 |
| 13–14 | 4e-07 | — | — | 50 | 100 | 1.85 |
| 15–16 | 4e-06 | — | — | 50 | 100 | 1.85 |
| 17–18 | 4e-05 | — | — | 50 | 100 | 1.85 |
| 19–20 | 4e-03 | — | — | 50 | 100 | 1.85 |
| 21–22 | 4e-03 | — | — | 50 | 100 | 1.85 |
| 23–24 | 4e-02 | — | — | 50 | 100 | 1.85 |

*Stock concentration [M] of compound to be tested.

Components are added in the following order: test compound, radioligand, buffer or tissue to give a final volume of 2.0 ml. After adding the tissue homogenate, the tubes are thoroughly mixed and incubated at 25° C. for 120 minutes. At the end of 120 minutes, the samples are filtered through GF/B glass fiber filters (Whatman) using a 24 sample cell harvester (Brandel) under a vacuum of 15 mm Hg. The tubes are washed with 5×3 ml ice-cold NaKPB. The filters are then placed in scintillation vials with 10 ml of scintillation cocktail (Beckman HP or HP/B), allowed to stand overnight, shaken and then counted. Specific binding is calculated as Total—NS (non-specific). The percent inhibition of specific binding is then calculated and the Ki values computed using either the LIGAND or LUNDON software packages for competition binding. The results of this test on representative compounds of this invention appear in Table I.

[$^3$H]-Cis-methyldioxolane Binding Assay (High Affinity)

This assay is utilized in conjunction with $^3$H-QNB binding to evaluate high affinity agonist binding and antagonist properties of CNS cholinergic agents. The procedure was adapted from Vickroy, T. W., Roeske, W. R, and Yamamura, H. I, J. Pharmacol. Exp. Ther. 229: 747–755 (1984). This is a rapid filtration assay that is set up to label only the high affinity agonist conformation of the muscarinic cholinergic receptor.

Tissue Preparation

Rats are sacrificed by decapitation and the brain removed and placed on ice. The cerebral cortex is dissected on a cold stage, weighed and homogenized (Polytron, setting 5.5 with PT-10 saw-tooth generator for 15 seconds) in 50 volumes (wet wt/vol) of ice-cold 10 mM (8.1 mM Na$_2$HPO$_4$, 1.9 mM KH$_2$PO$_4$) sodium-potassium phosphate buffer (NaKPB), pH 7.4. The homogenate is placed in an ice bath for 30 seconds and homogenized again as above. This procedure is repeated once again for a total of three times. The resulting homogenate is then diluted 1:3000 (original wet wt/vol) with icecold NaKPB for use in the assay. The final protein content per 2.0 ml of incubation mixture is 0.1 mg.

Dilution of Compounds

A stock solution of Atropine is prepared at 0.2 mM to define non-specific binding (11M final conc). Test compounds are prepared at 40 mM (final conc 1 mM) in buffer (if water soluble) or in absolute ethanol—1N HCl (1:1, v/v) and serially diluted to the desired concentrations. In general, dose-response profiles are examined between 1 mM and 1 pM final concentrations.

Preparation of $^3$H-CD $^3$H-CD (NEN, NET-647; specific activity=55.5 ci/mmol) is diluted to 20 nM with NaPB (final conc=1.0 nM, activity 75,000 cpm at a counting efficiency of 55%).

Technical Notes $^3$H-CD adheres readily to both glass and plastic surfaces. To eliminate this problem (and the chance for introducing artifacts into the results), stock vials, pipette tips and all glass tubes are routinely treated with Prosil-28, a siliconizing agent, and oven dried prior to use in an assay. Additionally, the GF/B glass fiber filters are pre-soaked in an aqueous polyethylenimine (PEI) solution (0.1%, pH 7.0) prior to use.

All points in the inhibition curve (including total and non-specific binding) are always measured on single PEI treated filter strips to minimize filter-to-filter variability. (See Bruns, R. F., et al. Anal. Biochem. 132: 74–81 (1983) for the use of PEI treated filters in filtration receptor assays).

The $^3$H-CD is prepared fresh in buffer just prior to use in the assay to avoid possible decomposition. It should be kept on an ice bath after dilution in buffer.

$^3$H-CD Binding Assay:

A typical protocol is outlined below:

| Tube No. | ID* | Buffer μL | Atropine μL | Test Compound μL | $^3$H—QNB μL | Tissue ml |
|---|---|---|---|---|---|---|
| 1–2 | Total | 50 | — | — | 100 | 1.85 |
| 3–4 | NS | 40 | 10 | — | 100 | 1.85 |
| 5–6 | 4e-11 | — | — | 50 | 100 | 1.85 |
| 7–8 | 4e-10 | — | — | 50 | 100 | 1.85 |
| 9–10 | 4e-09 | — | — | 50 | 100 | 1.85 |
| 11–12 | 4e-08 | — | — | 50 | 100 | 1.85 |
| 13–14 | 4e-07 | — | — | 50 | 100 | 1.85 |
| 15–16 | 4e-06 | — | — | 50 | 100 | 1.85 |
| 17–18 | 4e-05 | — | — | 50 | 100 | 1.85 |
| 19–20 | 4e-04 | — | — | 50 | 100 | 1.85 |
| 21–22 | 4e-03 | — | — | 50 | 100 | 1.85 |
| 23–24 | 4e-02 | — | — | 50 | 100 | 1.85 |

*Stock concentration [M] of compound to be tested.

Components are added in the following order: test compound, radioligand, buffer or tissue to give a final volume of 2.0 ml. After adding the tissue homogenate, the tubes are thoroughly mixed and incubated at 25° C. for 120 minutes. At the end of 120 minutes, the samples are filtered through GF/B glass fiber filters (Whatman) using a 24 sample cell harvester (Brandel) under a vacuum of 15 mm Hg. The tubes are washed with 5×3 ml ice-cold NaKPB. The filters are then placed in scintillation vials with 10 ml of scintillation cocktail (Beckman HP or HP/B), allowed to stand overnight, shaken and then counted. Specific binding is calculated as Total—NS (non-specific). The percent inhibition of specific binding is then calculated and the Ki values computed using either the LIGAND or LUNDON software packages for competition binding. The results of this test on representative compounds of this invention appear in Table I.

TABLE I

| | In vitro Binding Data | |
|---|---|---|
| Compound | $^3$H-QNB rat brain μM | $^3$H-CD rat brain μM |
| 1-[4-(1-Pyrrolidinyl)-2-butynyl 1H-pyrrole-2,5-dione | 0.2 | 0.029 |
| 3-Methyl-1-[4-(1-pyrrolidinyl)-2-butynyl]-1H-pyrrole-2,5-dione | 0.2 | 0.53 |
| 1-[4-Dimethylamino)-2-butynyl]-1H-pyrrole-2,5-dione | 1.74 | 1.48 |
| 1-[4-(Dimethylamino)-2-butynyl]-3-methyl-1H-pyrrole-2,5-dione | 1.4 | 3.4 |
| 4-(2,5-Dihydro-2,5-dioxo-1H-pyrrol-1-yl)-N,N,N-trimethy-2-butyne-1-aminium iodide | 11 | 0.29 |
| 4-(2,5-Dihydro-3-methyl-2,5-dioxo-1H-pyrrol-1-yl)-N,N,N-trimethyl-2-butyn-1-aminium iodide | 2.3 | 0.56 |
| 3-(Methylthio)-1-[4-(1-pyrrolidinyl)-2-butynyl]-2,5-pyrrolidinedione | 2.2 | 1.78 |
| 1-[4-(Dimethylamino)-2-butynyl]-3-(methylthio)-2,5-pyrrolidinedione | >100 | 1.6 |

Those compounds which have $^3$H-CD and $^3$H-QNB Ki values of less than 100 μM are considered active. The compounds tested can be divided into 3 categories:

(1) compounds which are products or therapeutic agents; (2) compounds which are a prodrug form of the products or therapeutic agents and (3) compounds which are reaction intermediates.

The pharmaceutical preparations of the present invention may contain, for example, from about 0.5% up to about 90% of the active ingredient in combination with the carrier, more usually between 5% and 60% by weight.

The effective dosage of active ingredient employed may vary with the particular compound employed, the mode of administration, and the severity of the condition being treated. In general, however, satisfactory results are obtained when the compounds of the invention are administered at a daily dosage of from about 0.02 mg to about 100 mg/kg of patient body weight, preferably given in divided doses two to four times a day, or in sustained release form. For most patients, the total daily dosage is from about 1 mg to about 5,000 mg, preferably from about 1 mg to 20 mg. Dosage forms suitable for internal use comprise from about 0.25 to 5.0 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

A decided practical advantage is that these active compounds may be administered orally as well as by intravenous, intramuscular, or subcutaneous routes if necessary. Solid carriers include starch, lactose, dicalcium phosphate, microcrystalline cellulose, sucrose, and kaolin, while liquid carriers include sterile water, polyethylene glycols, non-ionic surfactants, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, and antioxidants, e.g., vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under the conditions of manufacture and storage and must be preserved against the contaminating action of microorganisms such as bacteria and fungi. The carrier can be a solvent or dispersion medium containing, for example, water ethanol, polyol (e.g., glycerol, propylene glycol, and liquid polyethylene glycol), suitable mixtures thereof, and vegetable oils.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated.

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

2,2,2-Trifluoro-N-2-propynylacetamide

To a stirring 0° C. solution of 15.0 g of propargylamine in 200 ml of methylene chloride is added, dropwise, a solution of 63.0 g of trifluoroacetic anhydride in 50 ml of methylene chloride. The reaction is stirred at room temperature for 1 hour followed by the addition of 100 ml of water. The mixture is washed with 150 ml of 1N hydrochloric acid and 150 ml of saturated sodium bicarbonate. The organic layer is dried, filtered and concentrated in vacuo. The residue is distilled under vacuum (0.2 mmHg) at 40° C. to give 32.1 g of the desired product as a colorless oil.

EXAMPLE 2

2,2,2-Trifluoro-N-[4-(1-pyrrolidinyl)-2-butynyl]acetamide monohydrochloride

A mixture of 50.0 g of product from Example 1, 47.1 g of pyrrolidine, 24.9 g of paraformaldehyde, 50 ml of glacial acetic acid, 0.5 g of cuprous chloride and 500 ml of dry dioxane is heated at reflux temperature for 20 minutes. The reaction mixture is concentrated in vacuo and made basic to pH 10-11 with concentrated ammonium hydroxide. The aqueous layer is extracted with methylene chloride. The combined organic extracts are dried over sodium sulfate, filtered thru a pad of diatomaceous earth and concentrated in vacuo. The residue is distilled under vacuum (0.3 mm Hg) at 110°-120° C. to give the desired product as a yellow oil. Eight grams of oil is dissolved in 1N methanolic hydrogen chloride. The resulting solid is collected and recrystallized from methyl alcohol/diethyl ether to give 1.7 g of the desired product as the monohydrochloride.

Following the general procedure of Example 2 and using the product from Example 1, the products of Example 3-5, found in Table II, are prepared.

TABLE II

| Example | Reactant | Product | MP °C./or $[alpha]_D^{26°}$ methylene chloride |
|---|---|---|---|
| 3 | Dimethylamine | N-[4-(Dimethylamino-2-butynyl]-2,2,2-trifluoroacetamide mono-hydrochloride | 112–114° |
| 4 | Diethylamine | N-[Diethylamino)- | 111–112° |

TABLE II-continued

| Example | Reactant | Product | MP °C./or [alpha]$_D^{26°}$ methylene chloride |
|---|---|---|---|
| 5 | (S)-[2-[[[[(1,1-Dimethylethyl)-dimethylsilyl]-oxy]methyl]-1-pyrrolidinyl]-2-butynyl]-2,2,2-trifluoro-acetamide | 2-butynyl]-2,2,2-trifluoroacetamide mono-hydrochloride (S)-N-[4-[2-[[[(1,1-Dimethylethyl)-dimethylsilyl]oxy] methyl]-1-pyrro-lidinyl]-2-butynyl]-2,2,2-trifluoro-acetamide | −41 (C = 1.626%) methyl alcohol |

EXAMPLE 6

4-(1-pyrrolidinyl)-2-butyn-1-amine dihydrochloride

A mixture of 50.0 g of product from Example 2 and 267 ml of 4N hydrochloric acid is heated at reflux temperature. After 2 hours, the progress of the reaction is checked by thin layer chromatography, 70 ml of concentrated hydrochloric acid is added and the mixture is heated at reflux temperature overnight. The reaction is concentrated in vacuo and the residue is washed with methylene chloride. The aqueous layer is cooled, made basic with 10N sodium hydroxide and extracted with methylene chloride. The combined organic extracts are dried over sodium sulfate, filtered and concentrated in vacuo to give 27.8 g of a dark oil. The oil is treated with 450 ml of 1N methanolic hydrogen chloride and concentrated in vacuo. The resulting solid is recrystallized from methyl alcohol/diethyl ether to give 31.2 g of the desired product as off-white crystals.
mp 192°–193° C.

Following the general procedure of Example 6, the products of Example 7 and 8, found in Table III, are prepared.

TABLE III

| Example | Starting Material | Reactant | Product | MP °C./or [alpha]$_D^{26°}$ methylene chloride |
|---|---|---|---|---|
| 7 | Ex. 3 | HCL | N,N-Dimethyl-2-butyne-1,4-diamine dihydrochloride | 181–183° |
| 8 | Ex. 4 | HCL | N,N-Diethyl-2-1,4-diamine dihydrochloride | 149–150° |

EXAMPLE 9

(S)-4-[2-[[[(1,1-Dimethylethyl)dimethylsilyl]oxy]methyl]-1-pyrrolidinyl]-2-butyn-1-amine To a stirring solution of 5.76 g of product from Example 5 in 145 ml of tetrahydrofuan and 3 ml of water is added 5.76 g of sodium borohydride. The reaction is stirred at room temperature for 18 hours followed by concentration in vacuo to half volume. Saturated sodium sulfate is added and the mixture is extracted with methylene chloride. The organic layer is concentrated in vacuo to give a viscous oil. The oil is purified by chromatography (alumina, Grade 2.5, 1% methyl alcohol/methylene chloride) to give 1.92 g of the desired product as a colorless oil.
[a]$_D^{26}$ = −56 (methyl alcohol, C=1.016%).

EXAMPLE 10

(Z)-4-[[4-(Dimethylamino)-2-butynyl]amino]-4-oxo-2-butenoic acid

Three grams of product from Example 7 is partitioned between 4 ml of 10N sodium hydroxide and 100 ml of methylene chloride. The basic layer is saturated with sodium chloride and re-extracted with methylene chloride. The combined organic layers are dried, filtered and concentrated in vacuo to give the diamine base. The residue, dissolved in 150 ml of 1:1 methylene chloride:diethyl ether, is added, dropwise, with stirring, to 1.8 g of maleic anhydride in 30 ml of methylene chloride. The reaction is stirred at room temperature for 2 hours, filtered and recrystallized from acetonitrile to give 2.6 g of the desired product as colorless crystals. mp 155°–157° C.

Following the general procedure of Example 10, the products of Examples 11–19, found in Table IV, are prepared.

TABLE IV

| Example | Starting Material | Reactant | Product | MP °C./or [alpha]$_D^{26°}$ methylene chloride |
|---|---|---|---|---|
| 11 | Ex. 6 | Maleic anhydride | (Z)-4-Oxo-4[[4-(1-pyrrolidinyl-2-butynyl-]amino]-2-butenoic acid | 150–152° |
| 12 | Ex. 6 | Itaconic anhydride | 3-[[[(4-Pyrrolidinyl)-2-butynl]-amino] carbonyl]-3-butenoic acid | 102–104° |
| 13 | Ex. 7 | Itaconic anhydride | 3-[[[(4-Dimethylamino)-2-butynl]-amino] carbonyl]-3-butenoic acid | 146–148° |
| 14 | Ex. 8 | Maleic anhydride | 4-[[4-Dimethylamino)-2-butynl]-amino]-4-oxo-2-butenoic acid | 155–157° |
| 15 | Ex. 8 | Itaconic anhydride | (Z)-4-[[4-(Diethylamino)-2-butynyl]amino]methyl-4-oxo-2-butenoic acid | 126–128° |
| 16 | Ex. 9 | Maleic anhydride | (S-Z)-4-[[4-[2-[[(1,1-Dimethyl-ethyl)dimethyl-silyl]oxy]-1-pyrrolidinyl]-2-butynyl]amino]-4-oxo-2-butenoic acid | — |
| 17 | Ex. 11 | heat | 1-[4-(Pyrrolidinyl)-2-butynyl]-1H-pyrrole-2,5-dione | 160–170° (0.1 mm Hg) |
| 18 | Ex. 12 | heat | 3-Methyl-1-[4-(1-pyrrolidinyl)-2-butynyl]--1H-pyrrole-2,5-dione | 145–155° (0.1 mm Hg) |
| 19 | Ex. 16 | heat | (S)-1-[4-[2-[[(1,1-Dimethyl-ethyl) dimethylsilyl]oxy]-1-pyrrolidinyl]-2-butynyl]-1H-pyrrole-2,5-dione | — |

EXAMPLE 20

1-[4-(Dimethylamino)-2-butynyl]-1H-pyrrole-2,5-dione

A Kugelrohr oven apparatus is used to heat 1.25 g of product from Example 10 at 145°–180° C. (0.1 mm Hg) for 30 minutes. The distillate is dissolved in methylene chloride, dried over sodium sulfate, filtered and concentrated in vacuo to give 0.59 g of the product as a dark oil. The oil is redistilled at 130°–135° C. (0.05–0.075 mm Hg) to give 0.240 g of the desired product as a dark amber oil.
bp 130°–135° C. (0.05 mm Hg).

Following the general procedure of Example 20, the products of Example 21-23, found in Table V, are prepared.

TABLE V

| Example | Starting Material Sample # | Reactant | Product | BP °C. |
|---|---|---|---|---|
| 21 | Ex. 13 | heat | 1-[4-(Dimethylamino)-2-butynyl]-3-methyl-1H-pyrrole-2,5-dione | 145–155° (0.1 mm Hg) |
| 22 | Ex. 14 | heat | 1-[4-(Diethylamino)-2-butynyl]-1H-pyrrole-2,5-dione | |
| 23 | Ex. 15 | heat | 1-[4-(Diethylamino)-2-butynyl]-3-methyl-1H-pyrrole-2,5-dione | 140–150° (0.1 mm Hg) |

EXAMPLE 24

4-(2,5-Dihydro-3-methyl-2,5-dioxo-1H-pyrrol-1-yl)-N,N,N-trimethyl-2-butyne-1-aminium iodide A solution of 1.15 g of product from Example 21 in 25 ml of diethyl ether is treated with 0.6 ml of methyl iodide. The colorless crystals which precipitate are collected and dried. Recrystallization with acetonitrile/diethyl ether gives 1.0 g of the desired product. mp 168°–170° C.

Following the general procedure of Example 24, the product of Example 25, found in Table VI, is prepared.

TABLE VI

| Example | Starting Material Sample # | Reactant | Product | MP °C. |
|---|---|---|---|---|
| 25 | Ex. 17 | Methyl iodide | 4-(2,5-Dihydro-2,5-dioxo-1H-pyrrol-1-yl)-N,N,N-trimethyl-2-butyne-1-aminium iodide | 183–185° |

EXAMPLE 26

1-[4-(Dimethylamino)-2-butynyl]-3-(methylthio)-2,5-pyrrolidinedione

Methyl sulfide gas is bubbled, for 15 minutes, into a solution of 2.0 g of product from Example 21 in 25 ml of methylene chloride. The solution is allowed to stand at room temperature overnight. The reaction is concentrated in vacuo and the residue is chromatographed (alumina, Grade 2.5, 20% ethyl acetate/hexane) to give 0.785 g of the desired product as a yellow oil. CI-MS:m/z 241 (M+H).

Following the general procedure of Example 26, the product of Example 27, found in Table VII, is prepared.

TABLE VII

| Example | Starting Material Sample # | Reactant | Product | MP °C./ m/z M+ |
|---|---|---|---|---|
| 27 | 18 | Methylthiol | 3-(Methylthio)-1-[4-(1-pyrrolidinyl)-2-butynyl]-2,5-pyrrolidinedione | m/z MH+ 267 |

EXAMPLE 28

N,N,N-Trimethyl-4-[3(methylthio)-2,5-dioxo-1-pyrrolidinyl]-2-butyn-1-aminium iodide To a stirred room temperature solution of 0.24 g of product from Example 26 in 5 ml of 2-butanone is added 0.06 ml of methyl iodide in 5 ml of 2-butanone. The reaction mixture is stirred at room temperature overnight. Excess diethyl ether is added and the solvents are decanted from the product. Two ml of acetonitrile is added to the gummy residue and the mixture is warmed resulting in the formation of white crystal. Additional diethyl ether is added and the crystals are allowed to stand for 1 hour. The crystals are collected, washed with diethyl ether and dried to give 0.29 g of the desired product.
mp 157°–159° C.

EXAMPLE 29

1-(4-Bromo-2-butynl)-1H-pyrrole-2,5-dione

To a stirring 0° C. solution of product from Example 22 in 40 ml of diethyl ether is added, dropwise, 1.5 g of cyanogen bromide in 20 ml of diethyl ether. The reaction is stirred at 0° C. for 20 minutes and then stirred overnight at room temperature. The reaction is diluted with 50 ml of diethyl ether and extracted with 20 ml of 1N hydrochloric acid. The organic layer is rewashed with 1N hydrochloric acid and then with saturated sodium chloride. The diethyl ether layer is dried over sodium sulfate, filtered and concentrated in vacuo to give 2.6 g of an orange oil. The oil is purified by chromatography (silica gel, methylene chloride) to yield 1.63 g of the desired product as a light yellow oil which solidified on standing.
mp 60°–62° C.

We claim:

1. A compound selected from those of the formulae II and IV:

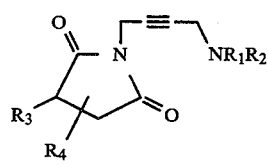

II

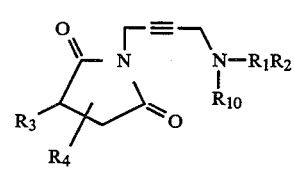

IV wherein $R_1$ and $R_2$ are independently selected from straight and branched ($C_1$–$C_6$)alkyl; or $R_1$ is selected from straight and branched ($C_1$–$C_6$)alkyl and $R_2$ is —$(CH_2)_n R_9$ where n=2–6 and $R_9$ is selected from hydroxy, ($C_1$–$C_{10}$)acyloxy, and trialkylsilyloxy or $R_1$ and $R_2$ taken together with their associated N(itrogen) are selected from the group consisting of pyrrolidine, piperidine and moieties of the formula:

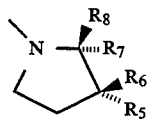

wherein $R_5$ and $R_6$ are independently selected from $(C_1-C_{10})$acyloxy, $(C_1-C_6)$alkoxy, aroyloxy, substituted aroyloxy (wherein the substituting moiety is selected from hydroxy, halo, alkyl $(C_1-C_6)$ and alkoxy $(C_1-C_6)$, hydroxy, thio, $(C_1-C_6)$alkylthio, $(C_1-C_6)$alkyldithio, $(C_1-C_{10})$acylthio and hydrogen; and $R_7$ and $R_8$ are selected from hydrogen, substituted methyl wherein the substituting moiety is selected from hydroxy, halo, $(C_1-C_6)$ alkylsulfonyloxy and phenylsulfonyloxy with the proviso that only one $R_5$, $R_6$, $R_7$, or $R_8$ can be a substituent other than hydrogen;

$R_3$ is selected from hydrogen, straight and branched $(C_1-C_6)$alkyl;

$R_4$ is selected from, straight and branched $(C_1-C_6)$ alkylthio;

$R_{10}$ is selected from $(C_1-C_6)$alkyl; and the pharmacologically acceptable salts thereof.

2. A compound according to claim 1, 1-[4-(dimethylamino)-2-butynyl]-3-(methylthio)-2,5-pyrrolidinedione.

3. A compound according to claim 1, 3-(methylthio)-1-[4(1-pyrrolidinyl)-2-butynyl]-2,5-pyrrolidinedione.

4. A compound according to claim 1, N,N,N-trimethyl-4-[3-(methylthio)-2,5-dioxo-1-pyrrolidinyl]-2-butyn-1-aminium iodide.

* * * * *